(12) United States Patent
Nagaike et al.

(10) Patent No.: US 11,944,570 B2
(45) Date of Patent: Apr. 2, 2024

(54) CHEMICAL BODY WARMER

(71) Applicant: KOBAYASHI PHARMACEUTICAL CO., LTD., Osaka (JP)

(72) Inventors: Daisaku Nagaike, Dalton, GA (US); Tsuyoshi Igaue, Ibaraki (JP)

(73) Assignee: Kobayashi Pharmaceutical Co., Ltd., Osaka (JP)

( * ) Notice: Subject to any disclaimer, the term of this patent is extended or adjusted under 35 U.S.C. 154(b) by 61 days.

(21) Appl. No.: 17/453,472

(22) Filed: Nov. 3, 2021

(65) Prior Publication Data
US 2022/0142815 A1    May 12, 2022

Related U.S. Application Data

(60) Provisional application No. 63/110,532, filed on Nov. 6, 2020.

(51) Int. Cl.
*A61F 7/03* (2006.01)
*A61F 7/00* (2006.01)
*A61F 7/02* (2006.01)

(52) U.S. Cl.
CPC ............ *A61F 7/034* (2013.01); *A61F 7/0097* (2013.01); *A61F 2007/0041* (2013.01); *A61F 2007/0042* (2013.01); *A61F 2007/0268* (2013.01); *A61F 2007/036* (2013.01)

(58) Field of Classification Search
CPC ...... A61F 2007/0041; A61F 2007/0042; A61F 2007/0268; A61F 2007/036; A61F 7/0097; A61F 7/034
See application file for complete search history.

(56) References Cited

U.S. PATENT DOCUMENTS

2009/0299442 A1\* 12/2009 Vergona ............... A47G 9/0215
                                                                 607/114
2010/0087902 A1\*  4/2010 Ota ........................ A61F 7/034
                                                                 156/250

FOREIGN PATENT DOCUMENTS

| JP | H03-031421 | 3/1991 |
| JP | 2005-171468 | 6/2005 |

OTHER PUBLICATIONS

International Search Report for PCT/JP2021/040866 dated Dec. 28, 2021 (in 2 pages).

\* cited by examiner

*Primary Examiner* — Tigist S Demie
(74) *Attorney, Agent, or Firm* — Knobbe Martens Olson & Bear LLP

(57) ABSTRACT

It is an object of the present invention to provide a chemical body warmer that achieves a sufficient heating effect even in a low-temperature environment at about 10° C. or less. A chemical body warmer including a flat housing including one or a plurality of cells each containing an exothermic composition that generates heat upon contact with air, wherein a total area of the cell or the plurality of cells in a plan view of the housing is 200 cm$^2$ or more, and the chemical body warmer is used by being placed under a blanket.

8 Claims, 5 Drawing Sheets

CHEMICAL BODY WARMER

TECHNICAL FIELD

The present invention relates to a chemical body warmer that achieves a sufficient heating effect even in a low-temperature environment at 10° C. or less.

BACKGROUND ART

Heating devices have been conventionally used to keep the body warm. Such heating devices include chemical body warmers (so-called disposable body warmers) in which air-permeable bags are filled with exothermic compositions that generate heat upon contact with oxygen; and electric blankets that generate heat by application of electric power. Because of their portability and convenience, chemical body warmers are in widespread use.

Chemical body warmers, however, are limited in their heat-generation temperatures because they utilize heat generated upon oxidation of an oxidizable metal, such as iron. For example, in mid-winter, events such as hunting or outdoor sports watching may take place in a low-temperature environment at about 10° C. or less (in particular, an extreme cold environment at about 0° C. or less). In such an environment, even chemical body warmers designed to be heated to a temperature as high as possible have had the disadvantage that the heat generated is taken away by the ambient air, and the desired heating effect cannot be achieved. For this reason, in a low-temperature environment at 10° C. or less (in particular, an extreme cold environment at 0° C. or less), only heat-generating devices that utilize electric power, such as electric blankets, have been usable, which is inconvenient because power generators or batteries are required to supply electric power outdoors.

SUMMARY OF INVENTION

Problem to be Solved by the Invention

It is an object of the present invention to provide a chemical body warmer that achieves a sufficient heating effect even in a low-temperature environment at about 10° C. or less.

Means for Solving the Problem

The present inventor conducted extensive research to solve the above-mentioned problem, and found that when a chemical body warmer including a flat housing including one or a plurality of cells each containing an exothermic composition that generates heat upon contact with air, wherein a total area of the cell or the plurality of cells in a plan view of the housing is 200 cm² or more, is used by being placed under a blanket, the chemical body warmer can achieve a sufficient heating effect even in a low-temperature environment at about 10° C. or less. The present invention has been completed by conducting further research based on this finding.

In summary, the present invention provides the below-listed embodiments of the invention:

Item 1. A chemical body warmer including a flat housing including one or a plurality of cells each containing an exothermic composition that generates heat upon contact with air, wherein a total area of the cell or the plurality of cells in a plan view of the housing is 200 cm² or more, and the chemical body warmer is used by being placed under a blanket.

Item 2. The chemical body warmer according to item 1, wherein the chemical body warmer exhibits a maximum reached temperature of 30° C. or more upon standing under a temperature condition of 0° C.

Item 3. The chemical body warmer according to item 1 or 2, wherein a total HGF value calculated based on equation (1) shown below is $4.0 \times 10^{6}$° C.·min·cm² or more:

$$\text{total HGF value (° C.·min·cm}^2\text{)} = A \times B, \quad \text{[Equation 1]}$$

where:
A: an area (° C.·min) of a region of 40° C. or more in a graph of time (min, horizontal axis) against heat-generation temperature (° C., vertical axis) obtained by measuring a temperature characteristic in accordance with a method defined in JIS S4100-1996 in the Japanese Industrial Standards; and
B: the total area (cm²) of the cell or the plurality of cells in plan view.

Item 4. The chemical body warmer according to any one of items 1 to 3, wherein a total amount of the exothermic composition contained in the housing is 70 to 1,000 g.

Item 5. The chemical body warmer according to any one of items 1 to 4, wherein the exothermic composition contains an oxidizable metal, and a total amount of the oxidizable metal contained in the housing is 20 to 800 g.

Item 6. The chemical body warmer according to any one of items 1 to 5, wherein the number of the cells provided in the housing is 2 to 20.

Item 7. The chemical body warmer according to any one of items 1 to 6, wherein the chemical body warmer is used by being placed on a lower limb.

Item 8. The chemical body warmer according to item 7, wherein the lower limb is a knee and/or a thigh.

Item 9. A method for warming a body, including placing the chemical body warmer according to any one of items 1 to 8 and a blanket in this order on a body region to warm the body.

ADVANTAGEOUS EFFECTS OF INVENTION

Figure 1:
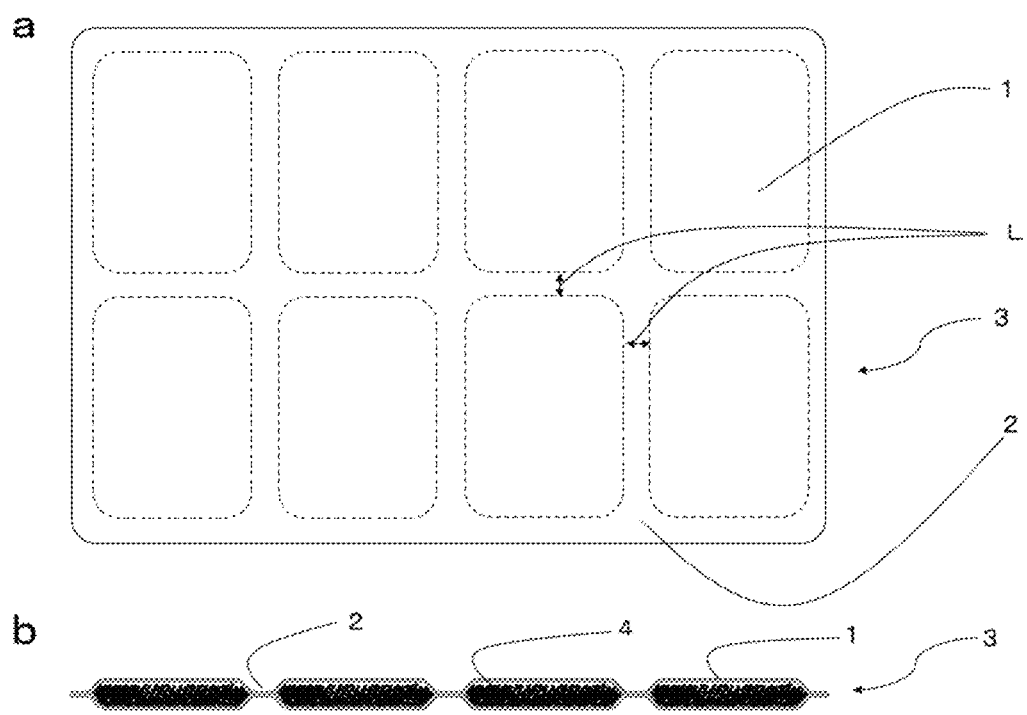
FIG. 1 shows a chemical body warmer of one embodiment of the present invention, in which (a) is a schematic diagram of a chemical body warmer 3 in elevation view, and (b) is a schematic cross-sectional view of the chemical body warmer 3 in a direction parallel to the long side thereof.

The chemical body warmer of the present invention, when used with a blanket, can achieve a sufficient warming effect even in a low-temperature environment at 10° C. or less (in particular, an extreme cold environment at 0° C. or less), and therefore, can effectively warm the body in, for example, events such as hunting or outdoor sports watching in midwinter.

Description of Embodiments

A chemical body warmer of the present invention includes a flat housing including one or a plurality of cells each containing an exothermic composition that generates heat upon contact with air, wherein a total area of the cell or the plurality of cells in a plan view of the housing is 200 cm² or more, and the chemical body warmer is used by being placed under a blanket. The chemical body warmer of the present invention will be hereinafter described in detail.

[Exothermic Composition]

The chemical body warmer of the present invention contains, as a heat-generating element, an exothermic composition that generates heat upon contact with oxygen.

The composition of the exothermic composition is not limited as long as it generates heat upon contact with oxygen, and may be any composition that is conventionally used for disposable body warmers and the like. One suitable example of the exothermic composition that generates heat upon contact with oxygen is a composition containing an oxidizable metal, an oxidation promoter, and water.

In the exothermic composition, the oxidizable metal is oxidized by contact with oxygen, and serves as a heat-generating source using oxidative heat. While the oxidizable metal is not limited in type as long as it can generate heat by oxidation, examples include metals such as iron (reduced iron, cast iron, atomized iron, and electrolytic iron), aluminum, zinc, manganese, magnesium, and calcium. These oxidizable metals may be used alone, or in combinations of two or more.

While the oxidizable metal is not limited in shape, the oxidizable metal is preferably in the form of a powder, granules, or fibers, and is more preferably in the form of a powder, from the viewpoint of heat-generation efficiency.

Among these oxidizable metals, an iron powder is preferred from the viewpoint of safety, handleability, and the like.

When the oxidizable metal is in the form of a powder, the particle diameter is, for example, 0.01 to 1,000 μm, preferably 0.1 to 500 μm, more preferably 0.5 to 300 μm, and still more preferably 30 to 250 μm, although not limited thereto.

As used herein, the particle diameter of the oxidizable metal in the form of a powder refers to the value measured in accordance with "dry sieving test" defined in JIS 8815-1994: "Test sieving—General requirements".

While the oxidizable metal content in the exothermic composition may be determined appropriately according to the heat-generation characteristic to be imparted, it is, for example, 20 to 80 wt %, preferably 25 to 70 wt %, and more preferably 45 to 60 wt %. In particular, when the oxidizable metal content in the exothermic composition is 45 to 60 wt %, the below-described maximum reached temperature and total HGF value tend to fall in preferred ranges, such that the chemical body warmer can achieve a markedly high heating effect in a low-temperature environment at 10° C. or less (in particular, an extreme cold environment at 0° C. or less).

In the exothermic composition, the oxidation promoter serves to hold oxygen, and supply oxygen to the oxidizable metal. While the oxidation promoter is not limited in type as long as it can hold oxygen and supply oxygen to the oxidizable metal, examples include carbon materials, such as activated carbon, carbon black, acetylene black, bamboo charcoal, wood charcoal, coffee grounds charcoal, graphite, coal, coconut husk charcoal, bituminous coal, peat, and lignite. These oxidation promoters may be used alone, or in combinations of two or more.

Among these oxidation promoters, activated carbon, carbon black, bamboo charcoal, wood charcoal, and coffee grounds charcoal are preferred, and activated carbon is more preferred.

While the oxidation promoter is not limited in shape, the oxidation promoter is preferably in the form of a powder, granules, or fibers, and is more preferably in the form of a powder, from the viewpoint of heat-generation efficiency.

When the oxidation promoter is in the form of a powder, the particle diameter is, for example, 0.001 to 1,000 μm, preferably 0.005 to 500 μm, and more preferably 0.01 to 200 μm, although not limited thereto. As used herein, the particle diameter of the oxidation promoter in the form of a powder refers to the value measured in accordance with "dry sieving test" defined in JIS 8815-1994: "Test sieving—General requirements".

While the oxidation promoter content in the exothermic composition may be determined appropriately according to the heat-generation characteristic and the like to be imparted, it is, for example, 1 to 30 wt %, preferably 3 to 25 wt %, and more preferably 4 to 25 wt %.

Furthermore, while the proportion of the oxidation promoter to the oxidizable metal in the exothermic composition may be determined appropriately according to the heat-generation characteristic to be imparted, the proportion of the oxidation promoter is, for example, 2 to 60 parts by weight, preferably 5 to 50 parts by weight, and more preferably 7 to 40 parts by weight, per 100 parts by weight of the oxidizable metal.

In the exothermic composition, water serves to oxidize the oxidizable metal together with oxygen. The water may be any of distilled water, ion-exchange water, pure water, ultrapure water, tap water, industrial water, and the like.

While the water content in the exothermic composition may be determined appropriately according to the heat-generation characteristic to be imparted, it is, for example, 5 to 50 wt %, preferably 10 to 40 wt %, and more preferably 15 to 35 wt %.

The exothermic composition may optionally contain a water-soluble salt, in addition to the above-described components. When the exothermic composition contains a water-soluble salt, the water-soluble salt can promote oxidation of the oxidizable metal.

While the water-soluble salt is not limited in type, examples include sulfates, hydrogen carbonates, chlorides, hydroxides, or the like of alkali metals (such as sodium and potassium), alkaline earth metals (such as calcium and magnesium), or heavy metals (such as iron, copper, aluminum, zinc, nickel, silver, and barium). Among these water-soluble salts, chlorides such as sodium chloride, potassium chloride, calcium chloride, magnesium chloride, and iron(II, III) chloride are preferred, and sodium chloride is more preferred, from the viewpoint of conductivity, chemical stability, and the like. These water-soluble salts may be used alone, or in combinations of two or more.

When the exothermic composition contains a water-soluble salt, the water-soluble salt content may be determined appropriately according to the heat-generation characteristic to be imparted; for example, the content is 0.1 to 10 wt %, preferably 0.5 to 7 wt %, and more preferably 1 to 5 wt %.

The exothermic composition may also optionally contain a water-retaining agent. The water-retaining agent serves to hold water, and supply the water to the oxidation reaction field.

Examples of types of the water-retaining agent include, although not limited to, inorganic porous materials, such as vermiculite, perlite, calcium silicate, magnesium silicate, kaolin, talc, smectite, mica, bentonite, calcium carbonate, silica gel, alumina, zeolite, silicon dioxide, and diatomaceous earth; organic materials, such as pulp, wood flour (sawdust), cotton, starches, and celluloses; and water-absorbing resins, such as polyacrylic acid-based resins, polysulfonic acid-based resins, maleic anhydride-based resins, polyacrylamide-based resins, polyvinyl alcohol-based resins, polyethylene oxide-based resins, polyaspartic acid-based resins, polyglutamic acid-based resins, and polyalginic acid-based resins. These water-retaining agents may be used alone, or in combinations of two or more.

Among these water-retaining agents, vermiculite, polyacrylic acid-based resins, wood flour, and pulp are preferred; and vermiculite and polyacrylic acid-based resins are more preferred. When an inorganic porous material is used as the water-retaining agent, it can ensure a path through which air flows in the exothermic composition.

The particle diameter of the water-retaining agent is, for example, 0.1 to 3,000 μm, preferably 0.5 to 1,000 μm, and more preferably 1 to 1,000 μm, although not limited thereto. As used herein, the particle diameter of the water-retaining agent refers to the value measured in accordance with "dry sieving test" defined in JIS 8815-1994: "Test sieving—General requirements".

When the exothermic composition contains the water-retaining agent, the water-retaining agent content may be determined appropriately according to the heat-generation characteristic to be imparted; for example, the content is 1 to 20 wt %, preferably 3 to 15 wt %, and more preferably 5 to 10 wt %.

The exothermic composition may also optionally contain other additives, such as metal-ion sequestering agents, fragrances, thickeners, excipients, surfactants, and hydrogen generation inhibitors.

The exothermic composition can be prepared by mixing the predetermined amounts of the above-described components. While the exothermic composition may be prepared in the presence of oxygen, it is preferably prepared under reduced pressure or an inert gas atmosphere.

[Structure of Housing]

The chemical body warmer of the present invention is formed by a flat housing including one or a plurality of cells each containing the above-described exothermic composition.

In the housing, the number of the cells containing the exothermic composition may be one, or two or more. However, the number of the cells is preferably plural, because if the number of the cells is one, and the total area of the cell falls in the range described below, the exothermic composition tends to be unevenly distributed in the cell. When the number of the cells provided in the housing is plural, the number may be determined appropriately according to the total area of the cells; for example, the number of the cells is 2 to 20, preferably 4 to 16, more preferably 6 to 12, still more preferably 6 to 10, and particularly preferably 8.

When the number of the cells provided in the housing is plural, the cells are preferably arranged such that they are evenly distributed in the housing, although the arrangement of the cells is not limited thereto.

The cells may have any of a polygonal shape, a circular shape, an oval shape, and the like in plan view, although the shape of the cells is not limited thereto. When the number of the cells provided in the housing is plural, all of the cells may have an identical shape, or the cells may be a combination of cells having two or more shapes.

When the number of the cells provided in the housing is plural, the cells preferably have a polygonal shape in plan view, and more preferably have a quadrilateral shape in plan view. When the number of the cells provided in the housing is plural, and the cells have a polygonal shape in plan view, the distance between mutually adjacent cells can be easily reduced, which facilitates achieving a heating effect uniformly throughout the housing.

In the chemical body warmer of the present invention, the total area of the cells in plan view is 200 $cm^2$ or more. Because the chemical body warmer of the present invention is designed such that the total area of the cells in plan view is as large as 200 $cm^2$ or more, it can achieve a sufficient heating effect even in a low-temperature environment at 10° C. or less (in particular, an extreme cold environment at 0° C. or less) when it is used by being placed under a blanket. As used herein, the total area of the cells in plan view refers to the total area of the region formed by the cells when observed from one surface of the flat housing. That is, when the number of the cells provided in the housing is only one, the above-defined total area refers to the area of the region formed by the one cell, and when the number of the cells provided in the housing is plural, the above-defined total area refers to the total area of the region of the plurality of cells.

In order to achieve a higher heating effect in a low-temperature environment at 10° C. or less (in particular, an extreme cold environment at 0° C. or less), the total area of the cells in plan view is preferably 200 to 2,000 $cm^2$, more preferably 400 to 1,500 $cm^2$, still more preferably 700 to 1,000 $cm^2$, and particularly preferably 700 to 900 $cm^2$. In particular, when the total area of the cells in plan view falls in the range of 700 to 1,000 $cm^2$, the chemical body warmer is suitable for use in keeping a lower limb, particularly a thigh and a knee, warm.

When the number of the cells provided in the housing is plural, the area per cell in plan view may be determined appropriately according to the number of the cells to have the above-described total area. In order to prevent the exothermic composition in the cells from being unevenly distributed, the area per cell in plan view is, for example, 30 to 200 cm$^2$, preferably 50 to 150 cm$^2$, and more preferably 80 to 130 cm$^2$.

In the plan view of the housing, the ratio of the total area of the cells to the area of the housing may be determined appropriately according to the number of the cells and the total area of the cells; for example, the ratio is 60 to 95%, preferably 65 to 90%, and more preferably 70 to 85%. The area of the housing refers to the total area of the housing in the plan view of the housing, that is, the total area of the region where the cells are provided and the region where the cells are not provided.

When the number of the cells provided in the housing is plural, the distance between adjacent cells in plan view is, for example, 0.5 to 2 cm, and preferably 0.5 to 1.5 cm. The distance between adjacent cells in plan view refers to the shortest distance between two adjacent cells, from an end of one cell to an end of the other cell.

While the area of the housing in plan view may be determined appropriately according to the total area of the cells, it is, for example, 210 to 2,500 cm$^2$, preferably 450 to 2,000 cm$^2$, and more preferably 800 to 1,200 cm$^2$.

While the housing may have any of a polygonal shape, a circular shape, an oval shape, and the like in plan view, it preferably has a polygonal shape in plan view, more preferably has a rectangular or square shape in plan view, and still more preferably has a rectangular shape in plan view, in terms of ease of use.

FIG. 1 shows a chemical body warmer of one preferred embodiment of the present invention. FIG. 1, (a) is a schematic diagram of a chemical body warmer 3 in plan view, and FIG. 1, (b) is a schematic cross-sectional view of the chemical body warmer 3 in a direction parallel to the long side thereof. The chemical body warmer 3 of the embodiment shown in FIG. 1 has a generally rectangular housing 2 in which eight cells 1 are provided. Four cells 1 are arranged in the direction parallel to the long side of the housing 2, and two cells 1 are arranged in a direction parallel to the short side of the housing 2. While the cells have a generally rectangular shape in the embodiment shown in FIG. 1, the cells may have other shapes, such as a polygonal shape, a circular shape, and an oval shape.

Specific shapes used in the embodiment shown in FIG. 1 are, for example, as follows: the area of the housing 2 in the plan view of the housing 2 is 500 to 2,000 cm$^2$, preferably 800 to 1,350 cm$^2$, and more preferably 850 to 1,300 cm$^2$; the long side of the housing 2 is 20 to 80 cm, preferably 30 to 50 cm, and more preferably 32 to 48 cm; the short side of the housing 2 is 0.3 to 0.99 times, preferably 0.5 to 0.8 times, and more preferably 0.6 to 0.7 times the long side; the total area of the cells 1 in the plan view of the housing 2 is 440 to 1,800 cm$^2$, preferably 660 to 1,100 cm$^2$, and more preferably 700 to 1,000 cm$^2$; the area per cell in plan view is 55 to 225 cm$^2$, preferably 81 to 138 cm$^2$, and more preferably 87 to 122 cm$^2$; the long side per cell is 6 to 25 cm, preferably 9 to 16 cm, and more preferably 10 to 15 cm; the short side per cell is 0.3 to 0.99 times, preferably 0.4 to 0.9 times, and more preferably 0.5 to 0.9 times the long side; in the plan view of the housing 2, the ratio of the total area of the cells 1 to the area of the housing 2 is 60 to 95%, preferably 65 to 90%, and more preferably 70 to 85%; and the distance L between adjacent cells is, for example, 0.5 to 2 cm, and preferably 0.5 to 1.5 cm.

Figure 2:
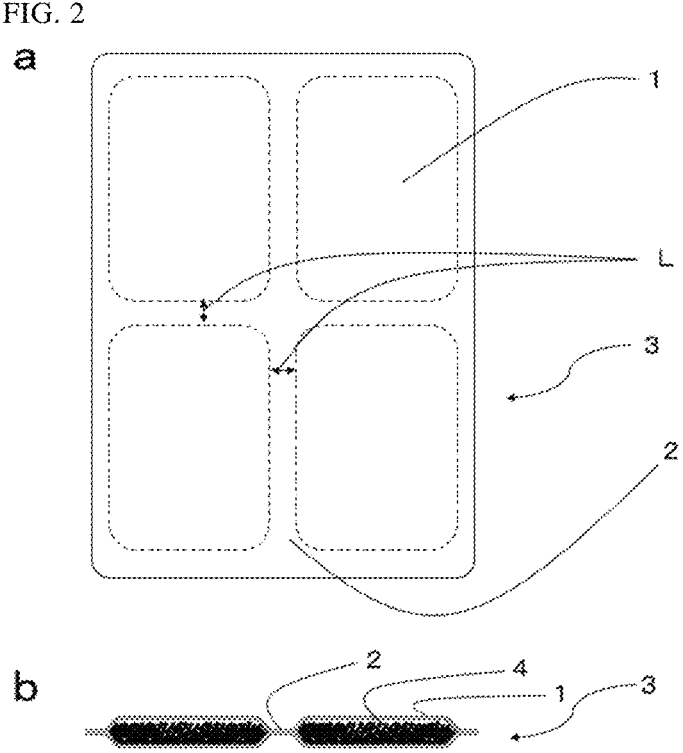
FIG. 2 shows a chemical body warmer of one embodiment of the present invention, in which (a) is a schematic diagram of a chemical body warmer 3 in elevation view, and (b) is a schematic cross-sectional view of the chemical body warmer 3 in a direction parallel to the short side thereof.

FIG. 2 shows a chemical body warmer of another embodiment of the present invention. FIG. 2, (a) is a schematic diagram of a chemical body warmer 3 in plan view, and FIG. 2, (b) is a schematic cross-sectional view of the chemical body warmer 3 in a direction parallel to the short side thereof. The chemical body warmer 3 of the embodiment shown in FIG. 2 has a generally rectangular housing in which four cells 1 are provided. Two cells are arranged in a direction parallel to the long side of the housing, and two cells are arranged in the direction parallel to the short side of the housing. While the cells have a generally rectangular shape in the embodiment shown in FIG. 2, the cells may have other shapes, such as a polygonal shape, a circular shape, and an oval shape.

Specific shapes used in the embodiment shown in FIG. 2 are, for example, as follows: the area of the housing 2 in the plan view of the housing 2 is 250 to 1,000 cm$^2$, preferably 400 to 675 cm$^2$, and more preferably 430 to 650 cm$^2$; the long side of the housing 2 is 20 to 80 cm, preferably 30 to 50 cm, and more preferably 32 to 48 cm; the short side of the housing 2 is 0.3 to 0.99 times, preferably 0.5 to 0.8 times, and more preferably 0.6 to 0.7 times the long side; the total area of the cells 1 in the plan view of the housing 2 is 220 to 900 cm$^2$, preferably 330 to 550 cm$^2$, and more preferably 350 to 500 cm$^2$; the area per cell in plan view is 55 to 225 cm$^2$, preferably 81 to 138 cm$^2$, and more preferably 87 to 122 cm$^2$; the long side per cell is 6 to 25 cm, preferably 9 to 16 cm, and more preferably 10 to 15 cm; the short side per cell is 0.3 to 0.99 times, preferably 0.4 to 0.9 times, and more preferably 0.5 to 0.9 times the long side; in the plan view of the housing 2, the ratio of the total area of the cells 1 to the area of the housing 2 is 60 to 95%, preferably 65 to 90%, and more preferably 70 to 85%; and the distance L between adjacent cells is, for example, 0.5 to 2 cm, and preferably 0.5 to 1.5 cm.

Figure 3:
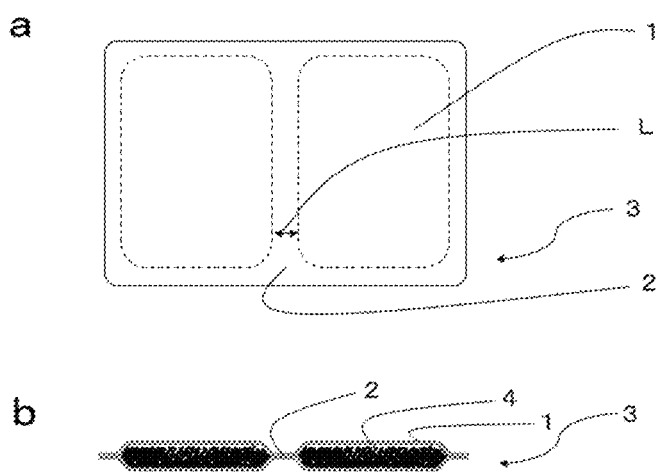
FIG. 3 shows a chemical body warmer of one embodiment of the present invention, in which (a) is a schematic diagram of a chemical body warmer 3 in elevation view, and (b) is a schematic cross-sectional view of the chemical body warmer 3 in a direction parallel to the long side thereof.

FIG. 3 shows a chemical body warmer of still another embodiment of the present invention. FIG. 3, (a) is a schematic diagram of a chemical body warmer 3 in plan view, and FIG. 3, (b) is a schematic cross-sectional view of the chemical body warmer 3 in a direction parallel to the long side thereof. The chemical body warmer 3 of the embodiment shown in FIG. 3 has a generally rectangular housing in which two cells are provided. The two cells are arranged in the direction parallel to the long side of the housing. While the cells have a generally rectangular shape in the embodiment shown in FIG. 3, the cells may have other shapes, such as a polygonal shape, a circular shape, and an oval shape.

Specific shapes used in the embodiment shown in FIG. 3 are, for example, as follows: the area of the housing 2 in the plan view of the housing 2 is 210 to 540 cm$^2$, preferably 230 to 340 cm$^2$, and more preferably 240 to 320 cm$^2$; the long side of the housing 2 is 15 to 24 cm, preferably 16 to 24 cm, and more preferably 18 to 22 cm; the short side of the housing 2 is 0.3 to 0.99 times, preferably 0.5 to 0.8 times, and more preferably 0.6 to 0.7 times the long side; the total area of the cells 1 in the plan view of the housing 2 is 200 to 330 cm$^2$, preferably 200 to 275 cm$^2$, and more preferably 210 to 250 cm$^2$; the area per cell in plan view is 100 to 165 cm$^2$, preferably 100 to 137.5 cm$^2$, and more preferably 105 to 125 cm$^2$; the long side per cell is 6 to 25 cm, preferably 9 to 19 cm, and more preferably 10 to 15 cm; the short side per cell is 0.3 to 0.99 times, preferably 0.4 to 0.9 times, and more preferably 0.5 to 0.9 times the long side; in the plan view of the housing 2, the ratio of the total area of the cells 1 to the area of the housing 2 is 60 to 95%, preferably 65 to 90%, and more preferably 70 to 85%; and the distance L between adjacent cells is, for example, 0.5 to 2 cm, and preferably 0.5 to 1.5 cm.

Figure 4:
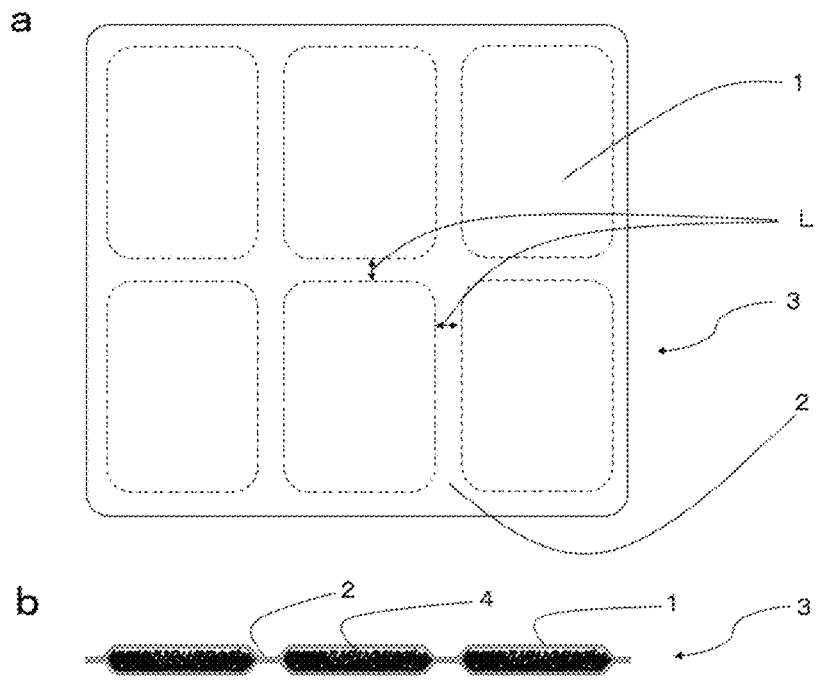
FIG. 4 shows a chemical body warmer of one embodiment of the present invention, in which (a) is a schematic diagram of a chemical body warmer 3 in elevation view, and (b) is a schematic cross-sectional view of the chemical body warmer 3 in a direction parallel to the long side thereof.

FIG. 4 shows a chemical body warmer of one preferred embodiment of the present invention. FIG. 4, (a) is a schematic diagram of a chemical body warmer 3 in plan view, and FIG. 4, (b) is a schematic cross-sectional view of the chemical body warmer 3 in a direction parallel to the long side thereof. The chemical body warmer 3 of the embodiment shown in FIG. 4 has a generally rectangular housing 2 in which six cells 1 are provided. Three cells 1 are arranged in the direction parallel to the long side of the housing 2, and two cells 1 are arranged in a direction parallel to the short side of the housing 2. While the cells have a generally rectangular shape in the embodiment shown in FIG. 4, the cells may have other shapes, such as a polygonal shape, a circular shape, and an oval shape.

Figure 5:
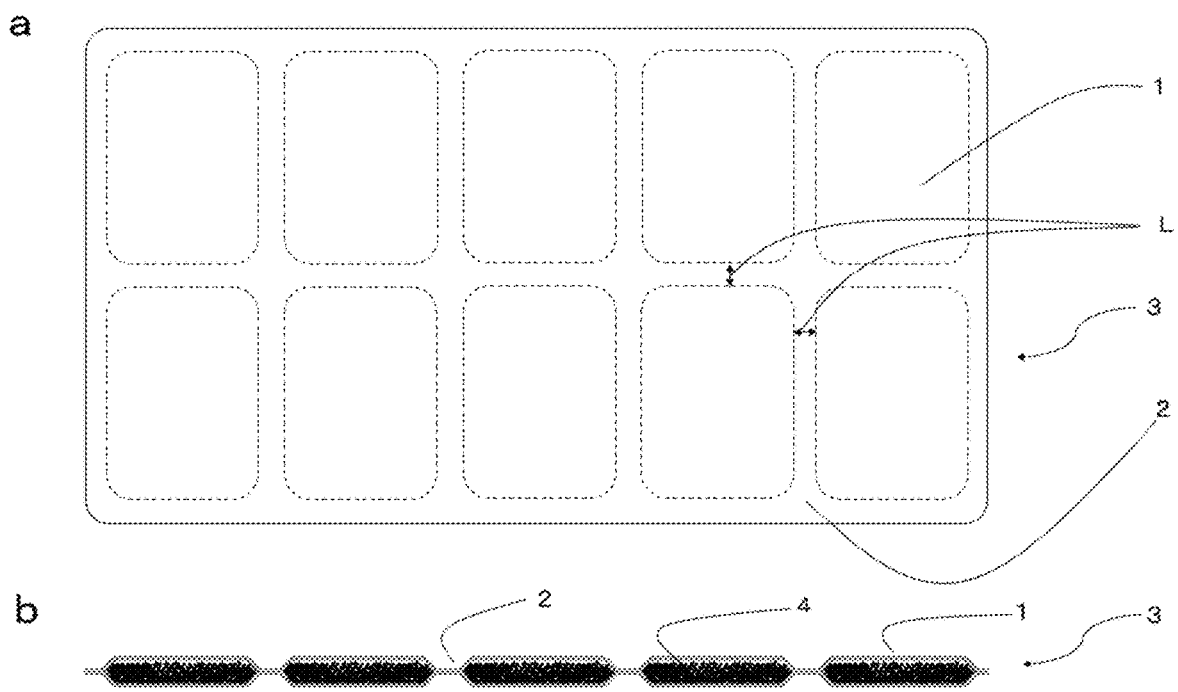
FIG. 5 shows a chemical body warmer of one embodiment of the present invention, in which (a) is a schematic diagram of a chemical body warmer 3 in elevation view, and (b) is a schematic cross-sectional view of the chemical body warmer 3 in a direction parallel to the long side thereof.

FIG. 5 shows a chemical body warmer of one preferred embodiment of the present invention. FIG. 5, (a) is a schematic diagram of a chemical body warmer 3 in plan view, and FIG. 5, (b) is a schematic cross-sectional view of the chemical body warmer 3 in a direction parallel to the long side thereof. The chemical body warmer 3 of the embodiment shown in FIG. 5 has a generally rectangular housing 2 in which ten cells 1 are provided. Five cells 1 are arranged in the direction parallel to the long side of the housing 2, and two cells 1 are arranged in a direction parallel to the short side of the housing 2. While the cells have a generally rectangular shape in the embodiment shown in FIG. 5, the cells may have other shapes, such as a polygonal shape, a circular shape, and an oval shape.

[Material of Housing]

The housing used in the chemical body warmer of the present invention may be any housing whose cell regions are air-permeable. At least one surface of the housing may be formed of an air-permeable sheet to render the cell regions air-permeable. That is, the two surfaces forming the housing may be formed of an air-permeable sheet, or one surface forming the housing may be formed of an air-permeable sheet, while the other surface forming the housing may be formed of an air-impermeable sheet.

The air-permeable sheet may be any of air-permeable sheets commonly used for housings of chemical body warmers, including, for example, air-permeable resin films, fibrous sheets, and laminated sheets thereof. In order to improve the feel in use, and prevent leakage of the exothermic composition, for example, the air-permeable sheet is preferably a laminated sheet of an air-permeable resin film and a fibrous sheet. When a laminated sheet of an air-permeable resin film and a fibrous sheet is used, the laminated sheet is preferably used such that the fibrous sheet is disposed on an outer surface of the chemical body warmer.

The air-permeable resin film may be a resin film provided with pores to ensure air permeability. The shape, size, and number of the pores provided in the resin film may be determined appropriately according to the air permeability to be imparted.

The resin constituting the air-permeable resin film is, for example, a thermoplastic resin, although not limited thereto. Specific examples of thermoplastic resins include polyethylene, polypropylene, ethylene-vinyl acetate copolymer, polyethylene terephthalate, polyacrylonitrile, ethylene-vinyl alcohol copolymer, polyamide, polyurethane, polystyrene, polyvinyl alcohol, polyvinyl chloride, polyvinylidene chloride, and polycarbonate. Among these thermoplastic resins, polyethylene, polypropylene, and ethylene-vinyl acetate copolymer are preferred. When the air-permeable resin film is formed of a polyolefin resin having heat fusibility, such as polyethylene or polypropylene, the air-permeable sheet can be provided with heat fusibility, which allows a housing having desired cells to be easily formed.

The air-permeable resin film has a thickness of, for example, 1 to 200 μm, and preferably has a thickness of 30 to 100 μm.

Specific examples of the fibrous sheet include nonwoven fabrics and woven fabrics. The fibrous sheet is preferably a nonwoven fabric, from the viewpoint of the feel in use. Examples of the material constituting the fibrous sheet include, although not limited to, synthetic fibers, such as polyethylene terephthalate, polybutylene terephthalate, nylon, polypropylene, polyethylene, vinylon, rayon, acryl, acetate, and polyvinyl chloride; natural fibers, such as cotton, hemp, silk, and paper; and mixtures of these fibers. Among these materials, polyethylene terephthalate, nylon, and polypropylene are preferred, and polyethylene terephthalate and nylon are more preferred, from the viewpoint of enhancing the feel in use.

The fibrous sheet has a weight per unit area of, for example, 1 to 100 g/m$^2$, preferably has a weight per unit area of 5 to 70 g/m$^2$, and more preferably has a weight per unit area of 10 to 50 g/m$^2$.

The laminated sheet of an air-permeable resin film and a fibrous sheet can be obtained by laminating the air-permeable resin film and the fibrous sheet, using a known lamination method, such as dry lamination, extrusion lamination, and thermal lamination.

The air permeability of the air-permeable sheet may be determined appropriately according to the type of the exothermic composition contained in the cells, the required heat-generation characteristic, and the like; for example, the air permeability is 1 to 100 sec/100 ml, preferably 2 to 50 sec/100 ml, more preferably 4 to 20 sec/100 ml, still more preferably 5 to 20 sec/100 ml, and particularly preferably 8 to 12 sec/100 ml. As used herein, the air permeability of the air-permeable sheet refers to the value measured in accordance with the method defined in JIS P8117:1988 in the Japanese Industrial Standards. Specifically, the air permeability refers to the value determined by measuring the time required for 100 cc of air to pass through, using a type B Gurely-type densometer, at a test area of 642 mm$^2$ and a cylinder weight of 567 g, in an atmosphere having a test temperature of 23° C. and a humidity of 50% RH.

The air-impermeable sheet may be an air-impermeable sheet including at least one air-impermeable resin film. The air-impermeable resin film may be a resin film not provided with pores, and the resin constituting the air-impermeable resin film is the same as described for the air-permeable resin film. The air-impermeable resin film has a thickness of, for example, 1 to 200 μm, and preferably has a thickness of 30 to 100 μm.

The air-impermeable sheet may also be optionally laminated with the above-described fibrous sheet besides the air-impermeable resin film. The air-impermeable sheet may also optionally include a polyolefin layer, such as polyethylene or polypropylene, as a layer forming the innermost surface of the housing. When the air-impermeable sheet includes a polyolefin layer, it can be provided with heat fusibility, which allows a housing having desired cells to be easily formed. The polyolefin layer has a thickness of, for example, 1 to 200 μm, and preferably has a thickness of 30 to 100 μm, although not limited thereto.

The housing optionally includes, on one surface, an adhesive layer that exhibits adhesive properties. The inclusion of the adhesive layer allows the chemical body warmer to be fixed to the body or clothing during use.

[Amount of Filled Exothermic Composition]

In the chemical body warmer of the present invention, the total amount of the exothermic composition contained in the housing may be determined appropriately according to the total area of the cells, the required heat-generation characteristic, and the like; it is, for example, 70 to 1,000 g. In order to achieve a higher heating effect in a low-temperature environment at 10° C. or less (in particular, an extreme cold environment at 0° C. or less), the total amount of the exothermic composition contained in the housing is preferably 100 to 500 g, and more preferably 200 to 400 g. When the number of the cells provided in the housing is one, the total amount of the exothermic composition contained in the housing refers to the amount of the exothermic composition filled in the one cell, and when the number of the cells provided in the housing is plural, the total amount of the exothermic composition contained in the housing refers to the total amount of the exothermic composition filled in the plurality of cells.

In the chemical body warmer of the present invention, the total amount of the oxidizable metal contained in the housing is, for example, 20 to 800 g. In order to achieve a higher heating effect in a low-temperature environment at 10° C. or less (in particular, an extreme cold environment at 0° C. or less), the total amount of the oxidizable metal contained in the housing is preferably 20 to 400 g, more preferably 40 to 250 g, still more preferably 60 to 200 g, and particularly preferably 100 to 200 g. When the number of the cells provided in the housing is one, the total amount of the oxidizable metal contained in the housing refers to the amount of the oxidizable metal contained in the exothermic composition filled in the one cell, and when the number of the cells provided in the housing is plural, the total amount of the oxidizable metal contained in the housing refers to the total amount of the oxidizable metal contained in the exothermic composition filled in the plurality of cells.

In the chemical body warmer of the present invention, the amount of the exothermic composition per unit area of the cells of the housing may be determined appropriately according to the total area of the cells and the amount of the exothermic composition filled in the cells; for example, the amount of the exothermic composition per unit area of the cells is 0.1 to 0.6 g/cm². In order to achieve a higher heating effect in a low-temperature environment at 10° C. or less (in particular, an extreme cold environment at 0° C. or less), the amount of the exothermic composition per unit area of the cells is preferably 0.3 to 0.5 g/cm². The amount of the exothermic composition per unit area of the cells refers to the value calculated by dividing the total amount (g) of the exothermic composition filled in the cells of the housing by the total area (cm²) of the cells in plan view.

In the chemical body warmer of the present invention, the amount of the oxidizable metal per unit area of the cells of the housing is, for example, 0.05 to 0.3 g/cm². In order to achieve a higher heating effect in a low-temperature environment at 10° C. or less (in particular, an extreme cold environment at 0° C. or less), the amount of the oxidizable metal per unit area of the cells of the housing is preferably 0.15 to 0.25 g/cm². The amount of the oxidizable metal per unit area of the cells of the housing refers to the value calculated by dividing the total amount (g) of the oxidizable metal contained in the exothermic composition filled in the cells of the housing by the total area (cm²) of the cells in plan view.

In the chemical body warmer of the present invention, when the number of the cells provided in the housing is plural, it is preferred that each cell be filled with an exothermic composition having an identical composition, and the amount of the exothermic composition per unit area of each cell be identical, in order to achieve a uniform heating effect throughout the chemical body warmer.

[Heat-Generation Characteristic]

As one exemplary heat-generation characteristic of the chemical body warmer of the present invention, the chemical body warmer exhibits a maximum reached temperature of 30° C. or more upon standing under a temperature condition of 0° C. Because the chemical body warmer of the present invention has this heat-generation characteristic, it can exhibit a higher heating effect when used by being placed under a blanket in a low-temperature environment at 10° C. or less (in particular, an extreme cold environment at 0° C. or less). In order to achieve a higher heating effect in a low-temperature environment at 10° C. or less (in particular, an extreme cold environment at 0° C. or less), the chemical body warmer of the present invention exhibits a maximum reached temperature of 30° C. or more, preferably 34 to 45° C., more preferably 36 to 44° C., and still more preferably 40 to 44° C., upon standing under a temperature condition of 0° C. The maximum reached temperature upon standing under a temperature condition of 0° C. refers to the maximum temperature determined as follows: Under a temperature condition of 0° C., the chemical body warmer is allowed to start generating heat with a central region of the cell of the housing of the chemical body warmer being placed on a temperature sensor fixed on a heat insulating material, and the temperature is measured with time. When the number of the cells provided in the housing is plural, the maximum reached temperature may fall in the above-defined range only for at least once cell. It is, however, preferred that the maximum reached temperature fall in the above-defined range for all of the cells.

As another exemplary heat-generation characteristic of the chemical body warmer of the present invention, the chemical body warmer exhibits a maximum reached temperature of 30° C. or more, preferably 34 to 44° C., more preferably 36 to 43° C. or more, still more preferably 39 to 43° C., and particularly preferably 41 to 43° C., upon standing under a temperature condition of −10° C. The maximum reached temperature upon standing under a temperature condition of −10° C. refers to the value measured under the same conditions as employed for the maximum reached temperature upon standing under a temperature condition of 0° C., except that the temperature condition is set to −10° C. When the number of the cells provided in the housing is plural, the maximum reached temperature may fall in the above-defined range only for at least once cell. It is, however, preferred that the maximum reached temperature fall in the above-defined range for all of the cells.

As still another exemplary heat-generation characteristic of the chemical body warmer of the present invention, the chemical body warmer exhibits a maximum reached temperature of 34° C. or more, preferably 37 to 50° C., more preferably 40 to 49° C., still more preferably 42 to 48° C., and particularly preferably 44 to 48° C., upon standing under a temperature condition of 10° C. The maximum reached temperature upon standing under a temperature condition of 10° C. refers to the value measured under the same conditions as employed for the maximum reached temperature upon standing under a temperature condition of 0° C., except that the temperature condition is set to 10° C. When the number of the cells provided in the housing is plural, the maximum reached temperature may fall in the above-defined range only for at least once cell. It is, however, preferred that the maximum reached temperature fall in the above-defined range for all of the cells.

As one preferred embodiment of a heat-generation characteristic of the chemical body warmer of the present invention, a total HGF (heat generation factor) value calculated based on equation (1) shown below is $4.0 \times 10^{6 \circ}$ C.·min·cm$^2$ or more. In order to achieve a higher heating effect in a low-temperature environment at 10° C. or less (in particular, an extreme cold environment at 0° C. or less), the total HGF value is preferably $7.0 \times 10^6$ to $1.0 \times 10^{8 \circ}$ C.·min·cm$^2$, more preferably $9.0 \times 10^6 \times 1.0 \times 10^{8 \circ}$ C.·min·cm$^2$, still more preferably $1.3 \times 10^7$ to $5.0 \times 10^{7 \circ}$ C.·min·cm$^2$, and particularly preferably $2.0 \times 10^7$ to $5.0 \times 10^{7 \circ}$ C.·min·cm$^2$.

$$\text{total HGF value (° C.·min·cm}^2\text{)} = A \times B, \quad \text{[Equation 1]}$$

where:
- A: an area (° C.·min) of a region of 40° C. or more in a graph of time (min, horizontal axis) against heat-generation temperature (° C., vertical axis) obtained by measuring a temperature characteristic in accordance with a method defined in JIS S4100-1996 in the Japanese Industrial Standards; and
- B: the total area (cm$^2$) of the cell or the plurality of cells in plan view.

Figure 6:
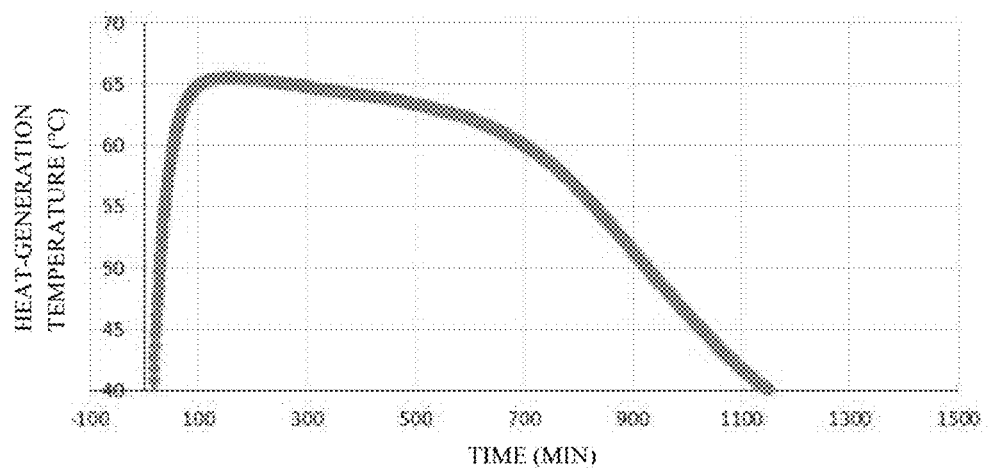
FIG. 6 shows a graph of time (min, horizontal axis) against heat-generation temperature (° C., vertical axis) in a heat-generation temperature range of 40° C. or more, obtained by measuring a temperature characteristic of the chemical body warmer of Example 1.

The value A may be calculated as follows: A temperature characteristic of the chemical body warmer is measured in accordance with the method defined in JIS S4100-1996 in the Japanese Industrial Standards, a graph of heat-generation temperature (° C., vertical axis) against elapsed time (min, horizontal axis) after the chemical body warmer is opened from the sealed bag is created, and the area (° C.·min) of the region of 40° C. or more in the graph is calculated. For reference, FIG. 6 shows a graph of time (min, horizontal axis) against heat-generation temperature (° C., vertical axis) in a heat-generation temperature range of 40° C. or more, obtained by measuring a temperature characteristic of the chemical body warmer of Example 1 described below, using the above-described method.

When the number of the cells provided in the housing is one, a temperature characteristic is measured for the central region of the cell in accordance with the method defined in JIS S4100-1996 in the Japanese Industrial Standards, the value A is determined, and the value A is multiplied by the area of the cell in plan view to calculate the total HGF value.

When the number of the cells provided in the housing is plural, and when each cell is filled with an exothermic composition having an identical composition, and the amount of the exothermic composition per unit area of each cell is identical, any one of the cells is selected, and for the central region of the cell, a temperature characteristic is measured in accordance with the method defined in JIS S4100-1996 in the Japanese Industrial Standards, the value A is determined, and the value A is multiplied by the total area of the cells in plan view to calculate the total HGF value.

When the number of the cells provided in the housing is plural, and when each cell is filled with an exothermic composition having a different composition, and the amount of the exothermic composition per unit area of each cell is different, temperature characteristics are measured for the central regions of all of the cells in accordance with the method defined in JIS S4100-1996 in the Japanese Industrial Standards, the values A are determined, each value A is multiplied by the area of the measured cell to calculate the HGF value for each cell, and the sum of the HGF values for all of the cells is calculated to calculate the total HGF value.

The means for adjusting the above-described heat-generation characteristic of the chemical body warmer of the present invention is known to a person skilled in the art. For example, the maximum reached temperature and the total HGF value may be adjusted to fall in the above-defined ranges by controlling, for example, the oxidizable metal content in the exothermic composition, the amount of the exothermic composition filled in the cells, the air permeability of the air-permeable sheet that forms the housing, the total area of the cells in plan view, and the like.

[Production Method]

The chemical body warmer of the present invention can be produced by laminating two sheets (one air-permeable sheet, or one air-permeable sheet and one air-impermeable sheet) that form the housing such that the predetermined amount of the exothermic composition is contained in the cells of a desired shape, and partially bonding the sheets. When at least one of the two sheets that form the housing includes a layer of a heat-sealable resin, such as a polyolefin, on the surface disposed on the inner side of the chemical body warmer, the two sheets can be partially bonded by application of heat and pressure. When neither of the two sheets that form the housing includes a layer of a heat-sealable resin, such as a polyolefin, on the surface disposed on the inner side of the chemical body warmer, the two sheets can be partially bonded using a heat-sealable resin, an adhesive, or the like. The region where the two sheets are not bonded forms the cells, while the region where the two sheets are bonded forms the region where the cells are not provided.

[Manner of Packaging]

The chemical body warmer of the present invention is provided in a state where it is contained in a sealed bag having oxygen barrier properties, such that the exothermic composition is prevented from contact with air. The sealed bag is opened prior to use, whereby the exothermic composition is contacted with air, and the chemical body warmer starts generating heat.

[Method of Use]

The chemical body warmer of the present invention is used by being placed on a body region, with a blanket being placed over the chemical body warmer. When the chemical body warmer of the present invention is used in such a manner that the chemical body warmer and a blanket are placed in this order on a body region, the chemical body warmer can achieve a sufficient heating effect even in a low-temperature environment at 10° C. or less (in particular, an extreme cold environment at 0° C. or less).

When the chemical body warmer of the present invention is placed on a body region, the chemical body warmer may be placed in direct contact with the skin, or may be placed with a garment intervening between the chemical body warmer and the skin.

Examples of the body region to which the chemical body warmer of the present invention is applied include, although not limited to, lower limb, back, shoulder, and neck. Among these body regions, a lower limb is preferred, and a knee and a thigh are more preferred.

The use environment of the chemical body warmer of the present invention is preferably a low-temperature environment at 10° C. or less, although it is not limited thereto as long as a heating effect is required. In particular, because the chemical body warmer of the present invention, when used with a blanket, can achieve a heating effect at 0° C. or less, specifically in an extreme-cold environment at −20 to 0° C., −15 to 0° C., or −10 to 0° C., it is suitably used in an environment at these temperatures.

Examples of the material of the blanket used during use of the chemical body warmer of the present invention include, although not limited to, natural fibers, such as cotton, linen, wool, cashmere, alpaca, angora, and camel; synthetic fibers, such as nylon, acryl, polyester, polyurethane, rayon, polynosic, and cuprammonium rayon; semi-synthetic fibers, such as cellulose fibers (such as acetate and triacetate) and protein fibers (such as promix); and combinations thereof.

The blanket has a thickness of, for example, 0.5 mm or more, preferably has a thickness of 0.5 to 100 mm, more preferably has a thickness of 1 to 50 mm, and still more preferably has a thickness of 1 to 30 mm.

The blanket preferably has a size such that it can cover the whole chemical body warmer of the present invention, although the size is not limited thereto.

EXAMPLES

The present invention will be hereinafter described in more detail with reference to examples, although the present invention is not limited thereto.

1. Preparation of Exothermic Composition

Exothermic compositions 1 and 2 having the compositions shown in Table 1 were prepared.

TABLE 1

|  | Exothermic Composition 1 | Exothermic Composition 2 |
| --- | --- | --- |
| Iron Powder | 50 | 30 |
| Activated Carbon | 15 | 25 |
| Vermiculite | 5 | 8 |
| Water-Absorbing Resin | 3 | 5 |
| Sodium Chloride | 1 | 2 |
| Water | 26 | 30 |
| Total (wt %) | 100 | 100 |

2. Air-Permeable Sheet

An air-permeable sheet I was prepared by laminating a nylon nonwoven fabric (weight per unit area: 50 g/m$^2$) and a polyethylene film (thickness: 50 μm; a film with pores).

An air-permeable sheet II was also prepared by laminating a nylon nonwoven fabric (weight per unit area: 50 g/m$^2$) and a polyethylene film (thickness: 50 μm; a film with pores).

The air permeability of each of these air-permeable sheets was measured in accordance with the method defined in JIS P8117:1988 in the Japanese Industrial Standards. As a result, the air permeability of the air-permeable sheet I was 10 sec/100 ml, and the air permeability of the air-permeable sheet II was 11.5 sec/100 ml.

3. Production of Chemical Body Warmer

Example 1

A chemical body warmer was produced to include a generally rectangular housing in which eight rectangular cells were provided, with each cell containing an exothermic composition. Specifically, the chemical body warmer was produced by using the exothermic composition 1, and heat-sealing two air-permeable sheets I such that the housing had the configuration shown in FIG. 1. All of the eight cells had an identical shape, and the amount of the exothermic composition contained in each cell was identical among all of the eight cells. The size of the housing, the size of the cells, the total area of the cells, the distance between adjacent cells, the total amounts of the exothermic composition and iron powder filled in the cells, the amounts of the exothermic composition and iron power per unit area of the cells, and the like are as shown in Table 2. The chemical body warmer produced was rapidly stored in a sealed bag.

Example 2

A chemical body warmer was produced to include a generally rectangular housing in which four rectangular cells were provided, with each cell containing an exothermic composition. Specifically, the chemical body warmer was produced by using the exothermic composition 1, and heat-sealing two air-permeable sheets I such that the housing had the configuration shown in FIG. 2. All of the four cells had an identical shape, and the amount of the exothermic composition contained in each cell was identical among all of the four cells. The size of the housing, the size of the cells, the total area of the cells, the distance between adjacent cells, the total amounts of the exothermic composition and iron powder filled in the cells, the amounts of the exothermic composition and iron power per unit area of the cells, and the like are as shown in Table 2. The chemical body warmer produced was rapidly stored in a sealed bag.

Example 3

A chemical body warmer was produced to include a generally rectangular housing in which four rectangular cells were provided, with each cell containing an exothermic composition. Specifically, the chemical body warmer was produced by using the exothermic composition 1, and heat-sealing two air-permeable sheets II such that the housing had the configuration shown in FIG. 2. All of the four cells had an identical shape, and the amount of the exothermic composition contained in each cell was identical among all of the four cells. The size of the housing, the size of the cells, the total area of the cells, the distance between adjacent cells, the total amounts of the exothermic composition and iron powder filled in the cells, the amounts of the exothermic composition and iron power per unit area of the cells, and the like are as shown in Table 2. The chemical body warmer produced was rapidly stored in a sealed bag.

Example 4

A chemical body warmer was produced to include a generally rectangular housing in which two rectangular cells were provided, with each cell containing an exothermic composition. Specifically, the chemical body warmer was produced by using the exothermic composition 1, and heat-sealing two air-permeable sheets I such that the housing had the configuration shown in FIG. 3. The two cells had an identical shape, and the amount of the exothermic composition contained in each cell was identical between both two cells. The size of the housing, the size of the cells, the total area of the cells, the distance between adjacent cells, the total amounts of the exothermic composition and iron powder filled in the cells, the amounts of the exothermic composition and iron power per unit area of the cells, and the like are as shown in Table 2. The chemical body warmer produced was rapidly stored in a sealed bag.

Example 5

A chemical body warmer was produced to include a generally rectangular housing in which four rectangular cells were provided, with each cell containing an exothermic composition. Specifically, the chemical body warmer was produced by using the exothermic composition 2, and heat-sealing two air-permeable sheets II such that the housing had the configuration shown in FIG. 2. All of the four cells had an identical shape, and the amount of the exothermic composition contained in each cell was identical among all of the four cells. The size of the housing, the size of the cells, the total area of the cells, the distance between adjacent cells, the total amounts of the exothermic composition and iron powder filled in the cells, the amounts of the exothermic composition and iron power per unit area of the cells, and the like are as shown in Table 2. The chemical body warmer produced was rapidly stored in a sealed bag.

4. Measurement of Maximum Reached Temperature

The maximum reached temperature of each of the chemical body warmers under a temperature condition of −10, 0, or 10° C. was measured by the following procedure: First, the chemical body warmer stored in the sealed bag and a thermometer (T&D temperature data logger, ONDOTORI TR-71WF; T&D Corporation) were allowed to stand on styrofoam (thickness: 50 mm), and acclimated for 2 hours or more under a temperature condition of −10, 0, or 10° C. Subsequently, with the temperature condition being maintained, the temperature sensor of the thermometer was fixed on the styrofoam, and then the center of one cell in the chemical body warmer opened from the sealed bag was placed on the temperature sensor. The temperature was then measured every one minute. The temperature measurement was conducted until generation of heat by the chemical body warmer was terminated. The highest temperature measured during that period was determined as the maximum reached temperature.

5. Measurement of Total HGF Value

A temperature characteristic of each of the chemical body warmers was measured in accordance with the method defined in JIS S4100-1996 in the Japanese Industrial Standards, and a graph of heat-generation temperature (° C., vertical axis) against time (min, horizontal axis) after the chemical body warmer was opened from the sealed bag was created. The area (° C.·min) of the region of 40° C. or more in the graph was calculated. The area (° C.·min) of the region of 40° C. or more was multiplied by the total area ($cm^2$) of the cells in each chemical body warmer to calculate the total HGF value (° C.·min·$cm^2$).

For reference, FIG. 6 shows a graph of time (min, horizontal axis) against heat-generation temperature (° C., vertical axis) in a heat-generation temperature range of 40° C. or more, obtained by measuring a temperature characteristic of the chemical body warmer of Example 1, using the above-described method.

6. Evaluation of Heat-Generation Characteristic with or without Use of Blanket The chemical body warmer of Example 1 was evaluated for its heat-generation characteristic at a temperature of −10, 0, or 10° C., with or without the use of a blanket. The specific procedure was as follows:

First, the chemical body warmer of Example 1 stored in the sealed bag, a blanket (made of polyester; length: 127 cm, width: 152 cm, thickness: 1.5 mm), and a thermometer (T&D temperature data logger, ONDOTORI TR-71WF; T&D Corporation) were allowed to stand on styrofoam (thickness: 50 mm), and acclimated for 2 hours or more under a temperature condition of −10, 0, or 10° C. Subsequently, with the temperature condition being maintained, the temperature sensor of the thermometer was fixed on the styrofoam, and then the center of one cell in the chemical body warmer opened from the sealed bag was placed on the temperature sensor. The blanket was then placed over the chemical body warmer. In this state, the temperature was measured every one minute for a total of 60 minutes. For comparison, the temperature was measured similarly, using the chemical body warmer of Example 1 only without using the blanket, or using the blanket only without using the chemical body warmer of Example 1, or using neither the chemical body warmer of Example 1 nor the blanket (ambient temperature).

7. Evaluation of Heating Effect in Actual Use

Subjects carrying each chemical body warmer stored in the sealed bag and a blanket (made of polyester; length: 127 cm, width: 152 cm, thickness: 1.5 mm) were allowed to enter a constant-temperature room set at a target temperature (−10, 0, or 10° C.), and acclimated for 1 hour while sitting. Thereafter, the chemical body warmer was opened from the sealed bag and placed on the thigh of each subject, and the blanket was then placed over the chemical body warmer. This state was maintained for 1 hour. The warm sensation perceived at that time was evaluated based on the criteria shown below. This test was conducted by two subjects, who made the evaluation based on the following criteria by consulting each other.

<Evaluation Criteria>

A: Sufficient heat was perceived.

B: Moderate heat was perceived.

C: Heat was perceived although it was somewhat insufficient.

D: Heat was perceived although it was weak.

E: No heat was perceived.

8. Test Results

Figure 7:
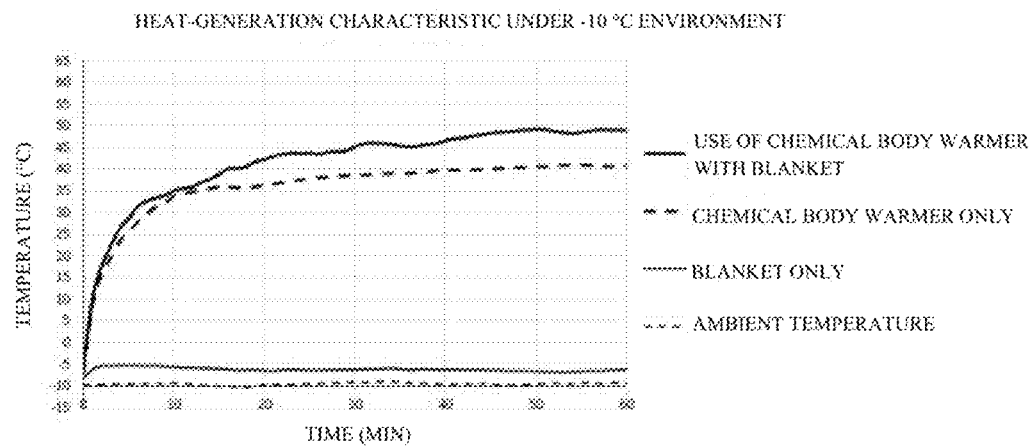
FIG. 7 shows the results of measuring a heat-generation characteristic of the chemical body warmer of Example 1 with or without the use of a blanket, in a −10° C. environment.
Figure 8:
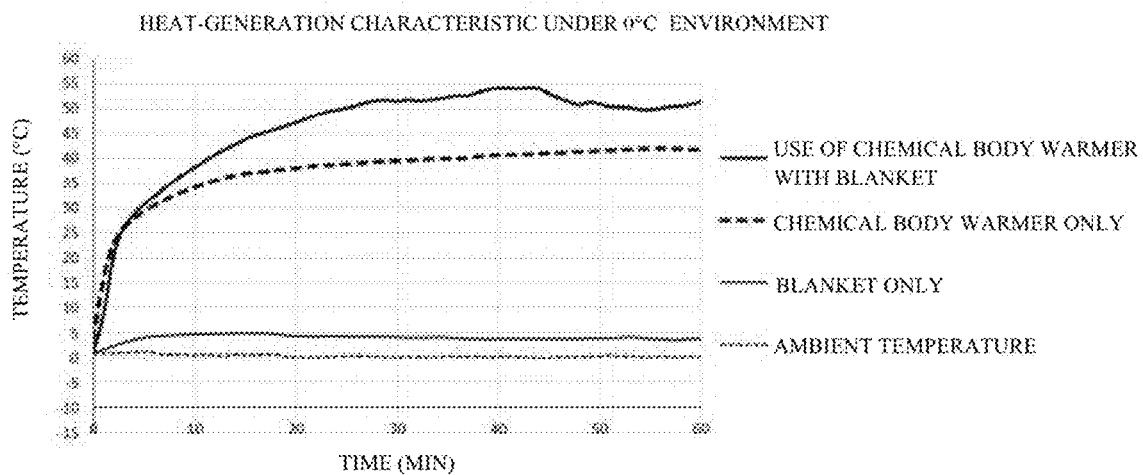
FIG. 8 shows the results of measuring a heat-generation characteristic of the chemical body warmer of Example 1 with or without the use of a blanket, in a 0° C. environment.
Figure 9:
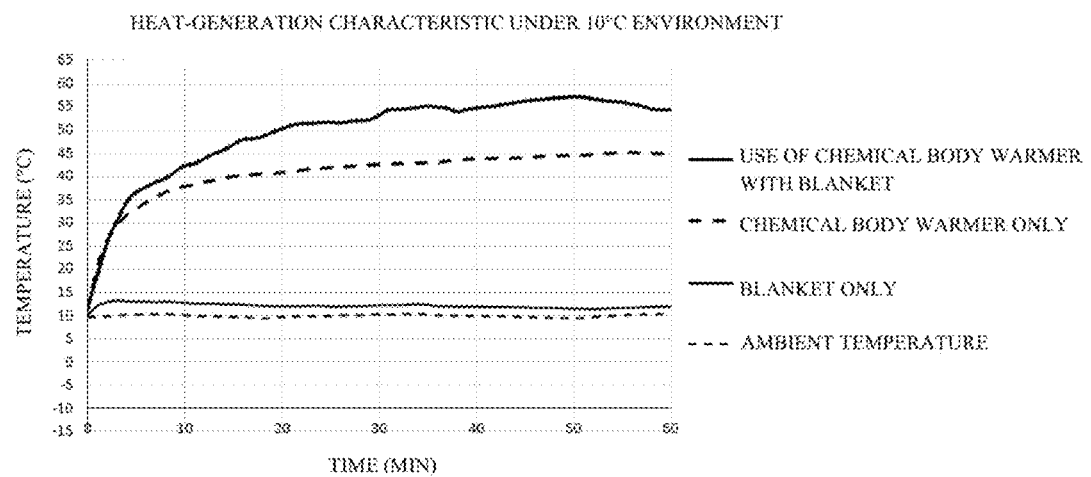
FIG. 9 shows the results of measuring a heat-generation characteristic of the chemical body warmer of Example 1 with or without the use of a blanket, in a 10° C. environment.

Table 2 shows the evaluation results of the maximum reached temperature, the total HGF value, and the heating effect in actual use for each of the chemical body warmers. FIGS. 7 to 9 each show the results of evaluating a heat-generation characteristic with or without the use of a blanket, at a temperature of −10° C., 0° C., or 10° C.

As a result, it was observed that a chemical body warmer whose total area of the cells is 200 $cm^2$ or more can impart heat when it is used by being placed under a blanket, under a temperature condition of −10 to 10° C. In particular, it was observed that when the chemical body warmer has a total HGF value of 7.0×$10^{6}$° C.·min·$cm^2$ or more and a maximum reached temperature of 34° C. or more at 0° C. without the use of blanket, the chemical body warmer can impart particularly high heat when it is used by being placed under a blanket, under a temperature condition of −10 to 10° C.

As shown in FIGS. 7 to 9, it was also confirmed that when the chemical body warmer of Example 1 is used with the blanket under a temperature condition of −10 to 10° C., the heat-generation temperature of the chemical body warmer is increased by as much as 5° C. or more.

TABLE 2

|  |  | Example 1 | Example 2 | Example 3 | Example 4 | Example 5 |
|---|---|---|---|---|---|---|
| Exothermic Composition | Type | 1 | 1 | 1 | 1 | 2 |
| Air-Permeable Sheet Housing | Type | I | I | II | I | II |
|  | Air Permeability (sec/100 ml) | 10 | 10 | 11.5 | 10 | 11.5 |
|  | Configuration | FIG. 1 | FIG. 2 | FIG. 2 | FIG. 3 | FIG. 2 |
|  | Housing Size (width × length) (cm) | 40 × 26.7 | 26.7 × 20 | 26.7 × 20 | 20 × 13.4 | 26.7 × 20 |
|  | Housing Area (cm$^2$) | 1068 | 534 | 534 | 268 | 534 |
|  | Number of Cells | 8 | 4 | 4 | 2 | 4 |
|  | Cell Size (width × length) (cm) | 12.4 × 8.9 | 12.4 × 8.9 | 12.4 × 8.9 | 12.4 × 8.9 | 12.4 × 8.9 |
|  | Total Area (cm$^2$) of Cells | 882.9 | 441.4 | 441.4 | 220.7 | 441.4 |
|  | Distance (cm) between Adjacent Cells | 1.1 | 1.1 | 1.1 | 1.1 | 1.1 |
|  | Ratio (%) of Total Area of Cells to Area of Housing | 83 | 83 | 83 | 82 | 83 |
|  | Total Amount (g) of Exothermic Composition Contained in Housing | 304 | 152 | 80 | 76 | 80 |
|  | Amount (g/cm$^2$) of Exothermic Composition per Unit Area of Cells | 0.4 | 0.4 | 0.2 | 0.4 | 0.2 |
|  | Total Amount (g) of Iron Powder Contained in Housing | 152 | 76 | 40 | 38 | 24 |
|  | Amount (g/cm$^2$) of Iron Powder per Unit Area of Cells | 0.20 | 0.20 | 0.11 | 0.20 | 0.06 |
| Maximum Reached Temperature | Temperature Condition: −10° C. | 41° C. | 37° C. | 34° C. | 31° C. | 30° C. |
|  | Temperature Condition: 0° C. | 42° C. | 39° C. | 35° C. | 33° C. | 32° C. |
|  | Temperature Condition: 10° C. | 45° C. | 42° C. | 37° C. | 36° C. | 34° C. |
| Total HGF Value (° C. · min · cm$^2$) |  | $2.2 \times 10^7$ | $1.2 \times 10^7$ | $8.0 \times 10^6$ | $5.9 \times 10^6$ | $4.3 \times 10^6$ |
| Evaluation Result of Warming Effect in Actual Use | Temperature Condition: −10° C. | A | B | C | D | D |
|  | Temperature Condition: 0° C. | A | B | C | D | D |
|  | Temperature Condition: 10° C. | A | A | C | C | C |

REFERENCE SIGNS LIST

1: Cell
2: Housing
3: Chemical body warmer
4: Exothermic composition
L: Distance between adjacent cells

What is claimed is:

1. A chemical body warmer comprising a flat housing comprising one or a plurality of cells each containing an exothermic composition that generates heat upon contact with air, wherein a total area of the cell or the plurality of cells in a plan view of the housing is 200 cm$^2$ or more, and the chemical body warmer is used by being placed under a blanket, wherein the chemical body warmer generates heat with a total heat generation factor (HGF) value calculated based on Equation (1) shown below that is $4.0 \times 10^{6}$ °C.·min·cm$^2$ or more:

$$\text{total HGF value (° C.·min·cm}^2) = A \times B, \quad [\text{Equation 1}]$$

where:
A: an area (° C.·min) of a region of 40° C. or more in a graph of time (min, horizontal axis) against heat-generation temperature (° C., vertical axis) obtained by measuring a temperature characteristic in accordance with a method defined in JIS S4100-1996 in the Japanese Industrial Standards; and
B: the total area (cm$^2$) of the cell or the plurality of cells in plan view.

2. The chemical body warmer according to claim 1, wherein the chemical body warmer exhibits a maximum reached temperature of 30° C. or more upon standing under a temperature condition of 0° C.

3. The chemical body warmer according to claim 1, wherein a total amount of the exothermic composition contained in the housing is 70 to 1,000 g.

4. The chemical body warmer according to claim 1, wherein the exothermic composition contains an oxidizable metal, and a total amount of the oxidizable metal contained in the housing is 20 to 800 g.

5. The chemical body warmer according to claim 1, wherein the number of the cells provided in the housing is 2 to 20.

6. The chemical body warmer according to claim 1, wherein the chemical body warmer is configured to be used by being placed on a lower limb.

7. The chemical body warmer according to claim 6, wherein the lower limb is a knee and/or a thigh.

8. A method for warming a body, comprising placing the chemical body warmer according to claim 1 and a blanket in this order on a body region to warm the body.

* * * * *